United States Patent [19]

Baker

[11] Patent Number: 4,600,006
[45] Date of Patent: Jul. 15, 1986

[54] CRANIAL PERFORATOR

[76] Inventor: John W. Baker, 4 Wachusett Dr., Acton, Mass. 01720

[21] Appl. No.: 575,571

[22] Filed: Jan. 31, 1984

[51] Int. Cl.⁴ .............................................. A61B 17/16
[52] U.S. Cl. .................................. 128/310; 128/305.1; 408/139
[58] Field of Search ............................ 128/305.1, 310; 408/139, 224, 225, 703

[56] References Cited

U.S. PATENT DOCUMENTS

| | | | |
|---|---|---|---|
| 881,865 | 3/1908 | Nichols | 128/310 |
| 1,043,408 | 11/1912 | Vilbiss | 128/305.1 |
| 2,842,131 | 7/1958 | Smith | 408/139 X |
| 4,148,593 | 4/1979 | Clark | 408/703 X |
| 4,319,577 | 3/1982 | Bofinger et al. | 128/305.1 |
| 4,456,010 | 6/1984 | Reimels et al. | 408/139 X |

Primary Examiner—Michael H. Thaler
Attorney, Agent, or Firm—Schiller & Pandiscio

[57] ABSTRACT

A new drill-type cranial perforator is disclosed of the type which comprises a front drill head assembly made up of a leading inner drill and a trailing outer drill, and a rear support and drive assembly adapted to enable both drills so long as the leading inner drill is encountering a resistive surface and to disable both drills when the leading inner drill stops encountering the resistive surface.

18 Claims, 13 Drawing Figures

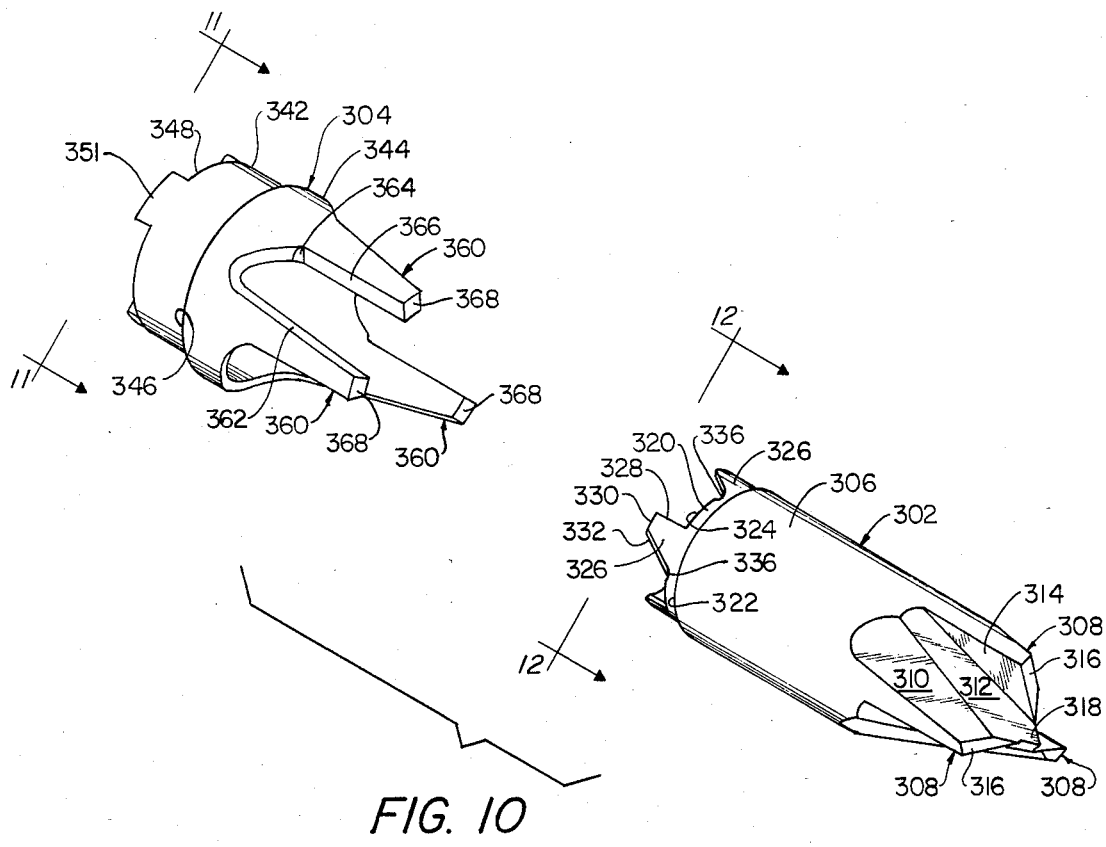
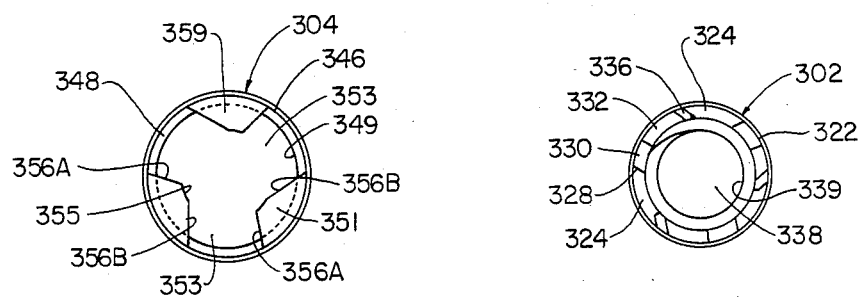
FIG. 10
FIG. 11    FIG. 12

CRANIAL PERFORATOR

FIELD OF THE INVENTION

This invention relates to drilling implements for use as surgical instruments, and more particularly to cranial perforators.

BACKGROUND OF THE INVENTION

Cranial perforators are special purpose drills which are used to bore holes through the skull during cranial surgery. Such holes may be needed to vent fluids from the region surrounding the brain, to provide small passageways to the brain for the insertion and removal of instruments, or to position a cranial saw for subsequent use in removing a larger piece of the skull.

Regardless of the end use of the hole being made, it is critical that the cranial perforator stop its boring action before it encounters—and thereby damages—the delicate dura tissue surrounding the brain, or the brain itself. To this end, cranial perforators have traditionally utilized a special "safety construction" designed to permit forward penetration by the perforator only so long as the perforator's leading tip is encountering hard bone, and to halt forward penetration by the perforator as soon as the perforator's leading tip passes through the hard bone and before it encounters the soft tissue beneath the bone. More particularly, cranial perforators have traditionally comprised a drill head assembly having a pair of drills disposed in concentric relation to one another, with the inner drill leading the outer drill slightly so that a bore-counterbore opening is formed as the perforator penetrates into the skull. The two drills are coupled to a rear support and drive assembly via a special clutch arrangement such that both drills are enabled so long as the leading inner drill is encountering a resistive surface (i.e., bone) and both drills are disabled as soon as the inner drill stops encountering the resistive surface (i.e., as soon as it passes through the bone). Inasmuch as the leading inner drill and trailing outer drill are adapted to cut in a bore-counterbore arrangement, the shoulder of bone formed at the intersection of the bore-counterbore opening impedes further progress of the perforator toward the brain once the leading inner drill is disabled. As a result, the surgeon using the cranial perforator can concentrate entirely on the placement of the cranial hole and need not fear that the perforator will penetrate too far into the head so as to damage the delicate dura tissue or the brain itself.

Cranial perforators using the aforementioned "safety construction" are believed to have been marketed by a number of different entities, among them Codman & Shurtleff of Randolph, Mass. (see U.S. Pat. No. 2842131), Aesculap of Tuttlengen, West Germany, and a medical instruments subsidiary of the 3M Corporation of Minneapolis, Minn. Such cranial perforators have included both reusable and disposable models.

Unfortunately, the cranial perforators developed prior to this invention are believed to suffer from one or more serious deficiencies. For example, some of the prior art cranial perforators are believed to be unreliable with regard to the operation of their special "safety construction". Such unreliability is intolerable since a failure of the "safety construction" to operate as intended can have catastrophic effects. At least some prior drill-type cranial perforators of the type described above have been prone to failure or to unreliable operation of their "safety construction" under non-axial loading. Because the prior safety construction usually involves a pair of diametrically-opposed members coupling the drill head assembly to the rear support and drive assembly, non-axial loading of the drill head assembly can give rise to a chattering action of sufficient magnitude to prematurely terminate the useful life of the safety construction of the perforator or to cause the safety construction to operate unreliably, e.g. possibly by intermittently disengaging the drill head assembly from the rear support and drive assembly. Other problems with prior art devices involve difficulty of manufacturing component parts with necessary precision, so that both quality and cost tend to suffer. Furthermore, it appears that virtually all or many prior art cranial perforators have proven difficult to center when starting a bore. This is particularly true when the bore site is well lubricated by blood or other fluids, so that the perforator has a tendency to skate or slip along the outside of the skull. This can result in unnecessary added injury to the patient. Also, at least some prior art cranial perforators tend to render unusable the cranial material removed from the bore site, with the result that the holes made by such perforators may have to be refilled with foreign materials at the close of surgery rather than with the patient's own bone matter. Also, most, if not all, prior art cranial perforators have required relatively high speed drilling (i.e., drilling at speeds of around 800-1000 RPM), which tends to be less desirable than low-speed drilling (i.e., drilling at speeds of around 100 RPM) for a variety of reasons.

In addition to the foregoing, in some prior art reusable cranial perforators, the rear support and drive assembly and/or the clutch means are inadequately designed to withstand repetitive non-axial loading, with the result that they fail after an indefinite period of use. Also, many prior art reusable cranial perforators are designed so that they must be disassembled into numerous pieces to effect proper cleaning, with the result that disassembly and subsequent reassembly tend to be fairly complicated and time-consuming. Moreover, with many prior art designs, if reassembly is improperly effected, the perforator's special "safety construction" may be rendered totally inoperative, in which case the perforator's forward penetration will not be halted automatically as soon as its leading tip passes through the skull, and damage to delicate tissues can ensue unless the surgeon is skillful and observant enough to prevent penetration into the dura.

In addition to the foregoing, disposable cranial perforators heretofore known have generally lacked safeguards to ensure that the perforator cannot be reused.

OBJECTS OF THE PRESENT INVENTION

Accordingly, one of the objects of the present invention is to provide a novel and improved drill-type cranial perforator having a reliable "safety construction" designed to permit forward penetration by the perforator only so long as the perforator's leading tip is encountering hard bone, and to halt forward penetration by the perforator as soon as the perforator's leading tip passes through the hard bone and before it encounters the soft tissue beneath the bone.

Another object is to provide a cranial perforator which has improved means for coupling the front drill head assembly to the rear support and drive assembly, so as to effectively assure automatic de-clutching of the drill head assembly from the support and drive assembly as the tip of the perforator penetrates the far side of the bone, even when the perforator is manipulated under non-axial loads.

Another object is to provide a cranial perforator which is relatively easy to manufacture with high precision tolerances.

Another object is to provide a cranial perforator which includes novel centering means to assist in centering the perforator when starting a bore, so as to minimize the tendency of the perforator to skate over the outer surface of the the skull.

Yet another object is to provide a cranial perforator which is adapted to remove bone material from a cranial opening in a form best suited for subsequent repacking in the opening when the opening is closed at the conclusion of surgery.

Still another object is to provide a cranial perforator which can be used with relatively slow speed drills (i.e., drills operating at speeds of around 100 RPM), as well as with relatively high speed drills (i.e., drills operating at speeds of around 800-1000 RPM).

A further object is to provide a reusable cranial perforator better adapted to withstand repetitive non-axial loading, so that the perforator will not tend to fail after an indefinite period of use.

Still another object is to provide a reusable cranial perforator which has a long operational lifetime, is easy to disassemble and to reassemble so as to facilitate cleaning, and which disassembles into relatively few pieces so as to facilitate dissassembly and reassembly.

Another object is to provide a reusable cranial perforator which will be rendered totally inoperative if it should be reassembled incorrectly.

A further object is to provide a disposable cranial perforator which cannot be disassembled without rendering the perforator totally inoperative.

Still another object is to provide a disposable cranial perforator which will indicate when it has been resterilized in an attempt to use it more than once.

And another object is to provide a novel drill which can be used to bore holes in various kinds of bone matter, e.g. cranial bone, breast bone, etc.

SUMMARY OF THE INVENTION

A new drill-type cranial perforator is disclosed of the type which comprises a front drill head assembly made up of a leading inner drill and a trailing outer drill, and a rear support and drive assembly adapted to enable both drills so long as the leading inner drill is encountering a surface offering a predetermined loading and to disable both drills when the leading inner drill stops encountering the predetermined loading. The new perforator is characterized by one or more of the following novel features: (1) a unique clutch arrangement coupling the front drill head assembly to the rear support and drive assembly and arranged so as to avoid decoupling and minimize stresses imposed by non-axially directed loading; (2) a novel centering means on the leading drill member to prevent "skating"; (3) a unique support and drive assembly designed to retard failure caused by repetitive non-axial loading; and (4) a unique support and drive assembly that prevents disassembly and reuse of the perforators. Other features and advantages are rendered obvious from the following detailed description.

BRIEF DESCRIPTION OF THE DRAWINGS

These and other objects and features of the present invention are more fully disclosed or rendered obvious by the following detailed description of the preferred embodiment of the invention, which is to be considered together with the accompanying drawings wherein like numbers refer to like parts, and further wherein:

FIG. 10 is an exploded perspective view of the drill head assembly of the same disposable cranial perforator;

FIG. 11 is a rear elevation of the outer drill of the same disposable cranial perforator, taken from the viewpoint represented by line 11—11 in FIG. 10;

FIG. 12 is a rear elevation of the inner drill of the same disposable cranial perforator, taken from the viewpoint represented by line 12—12 in FIG. 10.

DETAILED DESCRIPTION OF THE PREFERRED EMBODIMENT

Figure 1:
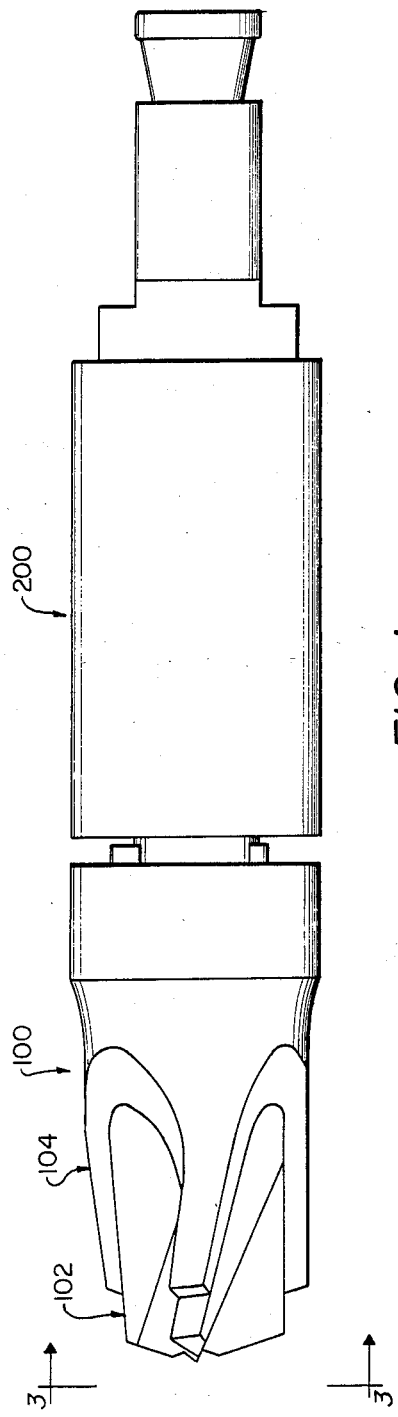
FIG. 1 is a side elevation of a reusable cranial perforator which comprises the preferred embodiment of the present invention.

Looking first at FIG. 1, there is shown a reusable cranial perforator constituting a preferred embodiment of the present invention. As seen in FIG. 1, the reusable cranial perforator generally comprises a front drill head assembly 100 and a rear support and drive assembly 200. Front drill head assembly 100 comprises an inner drill or drill member 102 and an outer drill or drill member 104.

Figure 2:
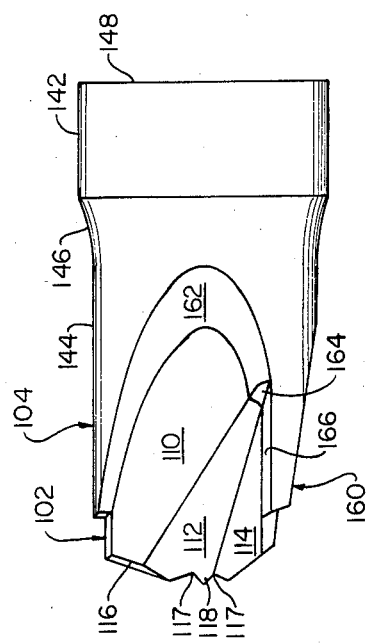
FIG. 2 is a side elevation of the drill head assembly of the same reusable cranial perforator rotated 60 degrees from the position shown in FIG. 1.
Figure 6:
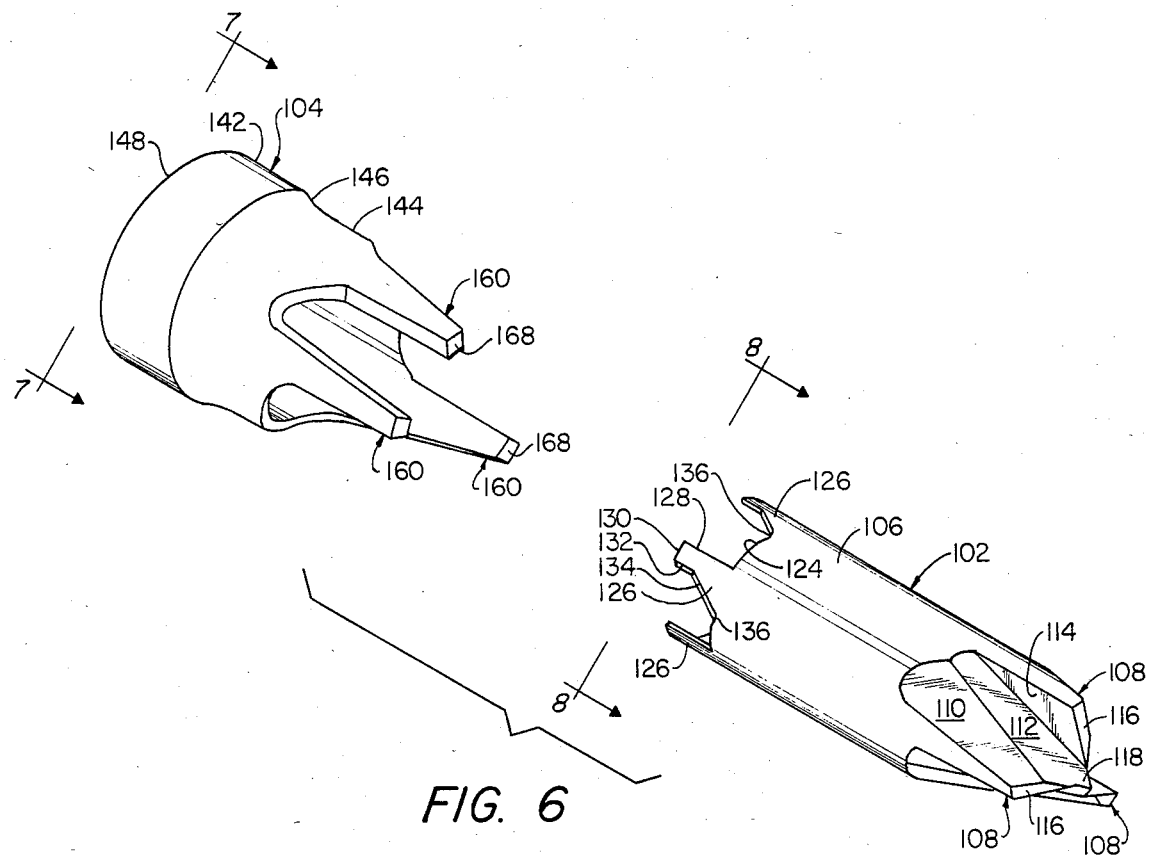
FIG. 6 is an exploded perspective view of the drill head assembly of the same reusuable cranial perforator.
Figure 7:
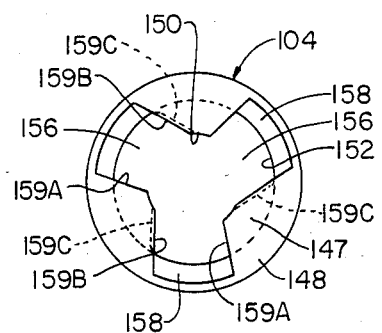
FIG. 7 is a rear elevation of the outer drill of the same reusuable cranial perforator, taken from the viewpoint represented by line 7—7 in FIG. 6.

Inner drill 102 is shown in FIGS. 1-4, 6 and 8. Drill 102 is generally cylindrical in nature and comprises a cylindrical midsection 106 (FIG. 6). The front end of drill 102 is dissected by a plurality of inclined intersecting surfaces so as to define three prismatic flutes or blades identified generally at 108. More particularly, the three flutes 108 comprise a trio of first inclined surfaces 110, a trio of second inclined surfaces 112, and a trio of third inclined surfaces 114, plus a trio of end surfaces 116, with each of the latter being intersected by surfaces 110 and 112 of one flute and surface 114 of another flute. Flutes 108 are disposed 120 degrees apart from one another. Accordingly, each of the surfaces 110, 112 and 114 of each flute is displaced 120 degrees from the corresponding surface of the other two flutes. On account of the relative dispositions of the inclined surfaces 110, 112, and 114, each of the flutes 108 includes a front end notch 117, and the inner drill terminates in a pyramidal end projection 118 which extends outward beyond the front end surfaces 116 of flutes 108 (FIGS. 2 and 6). The planes of surfaces 114 are eccentric to the lead point of pyramidal end projection 118, and end surfaces 116 are pitched at a 6½ degree angle in the circumferential (i.e., non-radial) direction. The leading edges of surfaces 116 constitute front cutting edges. The outer edges of surfaces 114 also constitute cutting edges.

Figure 4:
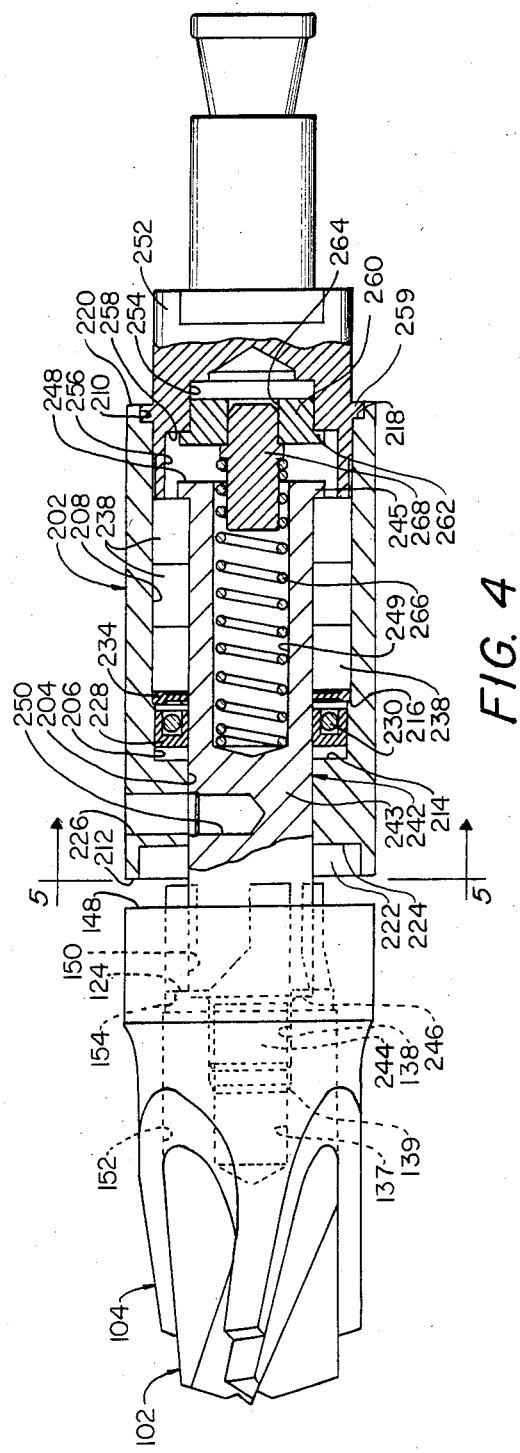
FIG. 4 is a side elevation, partially in section, of the same reusable cranial perforator, with the perforator's support and drive assembly rotated 90 degrees from the position shown in FIG. 1.
Figure 8:
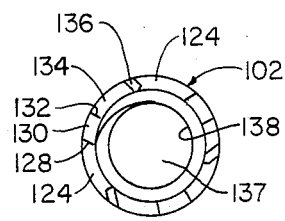
FIG. 8 is a rear elevation of the inner drill of the same reusuable cranial perforator, taken from the viewpoint represented by line 8—8 in FIG. 6.

The rear end of cylindrical midsection 106 terminates in an end surface or wall 124 (FIGS. 4, 6 and 8). A trio of lugs or keys or fingers 126 extend rearward from end surface 124. Rearwardly projecting lugs 126 are formed integral with cylindrical midsection 106 and are disposed 120 degrees apart from one another. Each of the lugs 126 is shaped so that it has a first side surface 128 which extends parallel to the center axis of drill member 102 and perpendicular to end surface 124, an end surface 130 which extends substantially parallel to end surface 124, a second side surface 132 which extends substantially perpendicular to end surface 124 (and end surface 130), and a third side surface 134 which extends at an inclined angle (i.e., non-perpendicular) to end surface 124. A small groove 136 is formed at the intersection of each inclined side surface 134 and end surface 124.

Inner drill 102 also includes an axial bore 137 which begins at rear end surface 124 of cylindrical midsection 106 and terminates in the middle of midsection 106, and a somewhat shallower threaded counterbore 138 which begins at rear end surface 124 of cylindrical midsection 106 and terminates at a shoulder 139 in the middle of midsection 106 (FIGS. 4 and 8).

Figure 3:
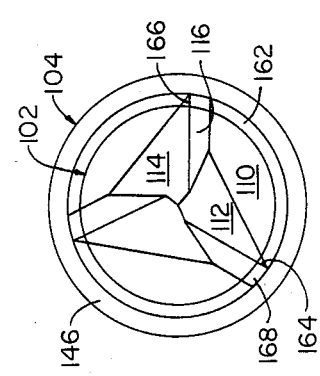
FIG. 3 is a front elevation of the same reusable cranial perforator, taken from the viewpoint represented by line 3—3 in FIG. 1.

Outer drill 104 is shown in FIGS. 1-4, 6 and 7. Outer drill 104 is generally cylindrical in nature, and is cut away in a selected manner so as to form a series of flutes or blades at its front end. More particularly, outer drill 104 comprises a substantially cylindrical rear section 142 which is joined to a generally cylindrical front section 144 by a substantially frustoconical section 146 (FIGS. 2, 3 and 6). Rear section 142 terminates in a rear surface 148 (FIGS. 2, 4, 6 and 7). Outer drill 104 includes an axial bore 152 (FIGS. 4 and 7), and three inwardly extending lips or dogs 147 having forward surfaces 154 (FIG. 4) and curved inside surfaces 150 which are arcs of a circle concentric to the axis of the outer drill. Outer drill 104 also includes a trio of slots 156 extending between lips 147. Slots 156 are spaced 120 degrees apart from one another. Each of the slots 156 forms a shoulder 158. Each of the lips 147 has side wall surfaces 159A and 159B. Lips 147 are bevelled away at their forward sides so that surfaces 159C extend between side wall surfaces 159B and forward surfaces 154. Surfaces 159C are planar in nature and extend at a 45 degree angle to side wall surfaces 159B and at a 45 degree angle to forward surfaces 154, for reasons which will hereinafter be made clear.

Referring next to FIGS. 1, 2, 3, 4, and 6, the outer drill's generally cylindrical front section 144 is dissected by a plurality of inclined intersecting surfaces so as to define three flutes or blades identified generally at 160. More particularly, the three flutes comprise a trio of first inclined surfaces 162, a trio of second inclined surfaces 164, and a trio of third inclined surfaces 166 (FIGS. 2 and 3). Flutes 160 are disposed 120 degrees apart from one another, and each terminates in a front end surface 168 (FIGS. 3 and 6). Front end surfaces 168 are pitched at a 3 degree angle in the circumferential (i.e., non-radial) direction. The leading edges of surfaces 168 are front cutting edges, while the outer edges of surfaces 166 constitute side cutting edges.

Inner drill 102 and outer drill 104 are assembled concentrically one inside the other so as to form the complete drill head assembly 100. More particularly, inner drill 102 and outer drill 104 are positioned in the manner shown in FIG. 6, i.e., so that the inner drill's flutes 108 are aligned with the outer drill's flutes 160, and so that the inner drill's lugs 126 are aligned with the outer drill's slots 156. Then the two drill members are brought together, so that the inner drill slips inside and makes a close sliding fit with the outer drill, with the inner drill's end wall 124 coming to rest against the forward surfaces 154 of lips 147 (FIG. 4). The various parts of the inner and outer drills are sized and shaped so that when the drill head assembly is put together with the inner drill's end surface 124 engaging the outer drill's surfaces 154, and the lugs 126 are located in slots 156, the outer drill's front end cutting surfaces 168 will be aligned with and behind the inner drill's front end surfaces 116, the outer drill's first inclined surfaces 162 will form a rearward extension of the inner drill's first inclined surfaces 110, the outer drill's second inclined surfaces 164 will form a rearward extension of the inner drill's second inclined surfaces 112, and the outer drill's third inclined surfaces 166 will form a rearward extension of the inner drill's third inclined surfaces 114 (FIGS. 2, 3 and 4). In addition, the inner drill's lugs 126 are sized so that when the inner drill's end wall 124 engages the outer drill's surfaces 154, the lugs 126 extend out through the outer drill's slots 156, with the lugs' first side surfaces 128 residing adjacent and parallel to side surfaces 159A of lips 147, and the lugs' inclined side surfaces 134 residing adjacent and parallel to bevelled surfaces 159C of lips 147. In addition, the inner drill's lugs 126 are sized so that they extend out beyond the outer drill's rear surface 148 when the inner drill's end wall 124 engages surfaces 154 of outer drill 104 (FIGS. 1 and 4).

It is to be appreciated that the foregoing assembly can be achieved only if inner drill 102 and outer drill 104 are properly aligned with one another (i.e., so that the inner drill's flutes 108 are aligned with the outer drill's flutes 160, and so that the inner drill's keys 126 are aligned with the outer drill's slots 156) prior to moving the two drills into engagement. On account of the size and shape of the inner drill's lugs 126 and the size and shape of outer drill 104, if the lugs 126 are not properly aligned with the outer drill's slots 156 when the two drill members are moved together, the end surfaces 130 of the inner drill's keys 126 will encounter the forward surfaces 154 of lips 147 and thereby prevent the inner and outer drills from achieving the position shown in FIG. 4.

Figure 5:
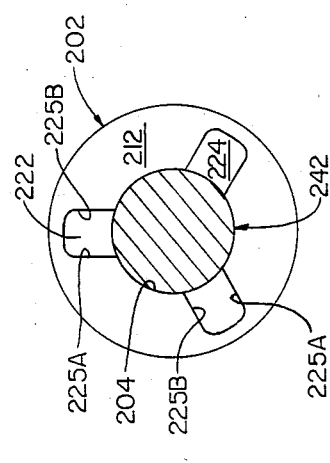
FIG. 5 is a cross-section of the same reusable cranial perforator, taken along line 5—5 of FIG. 4.

Rear support and drive assembly 200 is shown in FIGS. 1, 4 and 5. Assembly 200 comprises a cylindrical outer sleeve 202. Sleeve 202 includes an axial bore 204, a first axial counterbore 206, a second axial counterbore 208, and a third axial counterbore 210. Axial bore 204 begins at the sleeve's front end surface 212 and extends rearward to counterbore 206. A shoulder 214 is formed at the intersection of bore 204 and counterbore 206. Counterbore 206 in turn extends rearward to counterbore 208. A shoulder 216 is formed at the intersection of counterbore 206 and counterbore 208. Counterbore 208 extends rearward to counterbore 210. A shoulder 218 is formed at the intersection of counterbore 208 and counterbore 210. Counterbore 210 intersects the sleeve's rear end surface 220. Sleeve 202 also includes a trio of key-receiving recesses 222 formed in the sleeve's front end surface 212 (FIGS. 4 and 5). Recesses 222 are spaced 120 degrees apart from one another and have bottom surfaces 224. Each of the recesses 222 is defined by side wall surfaces 225A and 225B. A radial bore 226 extends through the side wall of sleeve 202.

An annular seal 228 (FIG. 4) is disposed within counterbore 206 concentric with the axis of sleeve 202. Seal 228 has a C-shaped cross-section and is formed out of a resilient material, e.g. a soft rubber. An expander element, e.g. a resilient 0-ring 230, is positioned inside the seal to keep it radially extended for the purpose hereinafter described.

An annular spacer element 234 is disposed within counterbore 208. Spacer element 234 rests against shoulder 216 and is sized so that its inner surface lies flush with the inner surface of sleeve 202.

Also disposed within counterbore 208 are three annular bearing members 238. Bearing members 238 are sized so that their innermost surfaces are flush with the surface of sleeve 202 which defines bore 204, and also with the innermost surface of spacer element 234.

A coupling or connecting pin 242 is slidably disposed within sleeve 202 and annular members 228, 234 and 238. Pin 242 is formed with a cylindrical midsection 243, a threaded cylindrical reduced diameter front section 244, and a rear flange 245 having an enlarged diameter relative to cylindrical midsection 243. A shoulder 246 is formed at the intersection of threaded cylindrical front section 244 and cylindrical midsection 243, and rear flange 245 terminates in an end surface 248. Connecting pin 242 is sized so that its cylindrical midsection 243 makes a close sliding fit in bore 204 of sleeve 202, and also with the innermost surfaces of seal 228 and spacer element 234 and bearings 238. As a result, connecting pin 242 is free to move independently of sleeve 202. At the same time, on account of the fact that the inside wall of seal 228 is urged by expander element 230 to assume a position slightly further inward than the surface of sleeve 202 which defines bore 204, resilient seal 228 engages and makes a good seal with the outer surface of the connecting pin's cylindrical midsection 243. This engagement is sufficient to prevent liquid or solid substances from passing between seal 228 and the connecting pin, but it is not sufficient to significantly inhibit the movement of connecting pin 242 relative to sleeve 202. Connecting pin 242 also includes an axial bore 249 which begins at its rear surface 248 and extends into the pin's cylindrical midsection, and a radial bore 250 which begins at the pin's outside surface and extends into midsection 243. Radial bore 250 is positioned so that it will be aligned with the sleeve's bore 226 when the connecting pin's rear flange 245 is in engagement with the rearmost bearing 238, and radial bore 250 has a diameter identical to the diameter of radial bore 226.

Means are provided to urge connecting pin 242 forward so that the pin's rear flange 245 normally engages the rearmost bearing 238, in the manner shown in FIG. 4. More particularly, the rear support and drive unit 200 includes a drive adapter 252 which closes off the rear of sleeve 202. Adapter 252 has a stepped-down exterior configuration at its rear end which is adapted to be received by a Hudson chuck, as will hereinafter be described in further detail. Adapter 252 includes an axial bore 254, an axial counterbore 256, a shoulder 258 formed at the intersection of bore 254 and counterbore 256, and a peripheral flange 259. Adapter 252 is press fitted into the sleeve's counterbore 208, with its peripheral flange 259 making a close fit in the sleeve's counterbore 210. The inner end of adapter 252 engages the rearmost bearing 238 and thereby captivates the bearings in sleeve 202. A thrust bearing unit 260 having a circular peripheral flange 262 is disposed in the end cap's bore 254 and counterbore 256, in the manner shown in FIG. 4. Bearing unit 260 includes an axial through-hole 264 which accommodates a mandrel or spring pin 268 which serves as an anchor for a compression spring 266. The latter extends into bore 249 of pin 242. This construction suffices to keep the connecting pin's rear flange 245 biased against the rearmost bearing member 238, without significantly impeding the rotation of connecting pin 242 relative to sleeve 202. At the same time, pin 242 is capable of axial motion relative to sleeve 202 to the extent permitted by the gap normally residing between the pin's flange 245 and thrust bearing 260.

It will be appreciated that rear support and drive assembly 200 essentially forms a self-contained unit wherein connecting pin 242 projects its threaded front end 244 outward from the front end of sleeve 202 and is yieldably biased into that position, and further wherein the connecting pin is capable of rotation relative to sleeve 202.

The front drill head assembly 100 is united with the rear support and drive assembly 200 by screwing the connecting pin's threaded cylindrical front section 244 into the inner drill's threaded counterbore 138, so that the connecting pin's shoulder 246 engages the inner drill's end surface 124.

The various parts of the cranial perforator are sized so that the drill head assembly can only be screwed onto connecting pin 242 when the inner drill's lugs 126 extend through the outer drill's slots 156, for reasons which will hereinafter be described in detail. In addition, the various parts of the cranial perforator are sized so that when the drill head assembly and the support and drive assembly are so united, and the connecting pin's rear flange 245 is in engagement with the rearmost bearing unit 238, the inner drill's lugs 126 will terminate short of the sleeve's front end surface 212 (FIG. 4). At such time, the lugs are incapable of being locked to sleeve 202 so that sleeve 202 cannot drive the drill head assembly. At the same time, however, the various parts of the cranial perforator are sized so that when the front drill head assembly and the rear support and drive assembly are united in the foregoing manner, and the inner drill 102 is thereafter forced rearwardly relative to sleeve 202 against the action of spring 266, the lugs 126 can extend into the key-receiving recesses 222 before the connecting pin's rear surface 248 contacts bearing unit 260, whereby the lugs can lock the drill head assembly to the sleeve so as to cause the two to rotate together.

Operation of the cranial perforator will now be described.

The assembled cranial perforator is prepared for use by fitting the perforator's adaptor 252 into a Hudson chuck which is disposed on the end of the drive shaft of a suitable driver. Subsequent rotation of the drive shaft in a counterclockwise direction (as viewed in FIG. 3)

will cause the rear support and drive unit 200 to rotate in the same counterclockwise direction. On account of some residual friction between connecting pin 242 and the remainder of the rear support and drive unit 200, the front drill head assembly 100 will generally tend to rotate with rear support and drive unit 200 so long as the front drill head assembly is not encumbered by any braking action. However, if any braking action whatsoever is applied to inner drill 102 while the rear support and drive unit 200 is rotating, without the inner drill being subjected to a rearward force sufficient to overcome the force of spring 266, the perforator's aforementioned construction will allow front drill head assembly 100 to stop rotating even while rear support and drive unit 200 continues to rotate. Similarly, if any braking action is applied to outer drill 104 while the rear support and drive unit 200 is rotating and while the inner drill is not subjected to a rearward force sufficient to overcome the force of spring 266, the non-rotating outer drill will be cammed backward by virtue of the engagement of the inclined surfaces 134 of lugs 126 with surfaces 159C of lips 147, until the outer drill's rear end surface 148 contacts the sleeve's front end surface 212, and while so positioned the outer drill will be in sliding engagement with the rotating sleeve. As soon as the outer drill's surfaces 159B contact side surfaces 132 of the inner drill's lugs 126, rotation of the inner drill will also cease, the continued rotation of the rear support and drive unit 200 notwithstanding.

Now when the cranial perforator is to be used to drill a hole in a skull, the powered drive unit (not shown) drives the cranial perforator in a counterclockwise direction. The cranial perforator is brought down so that its pyramidal front projection 118 contacts the skull precisely where the cranial hole is to be made. As the sharp pyramidal projection 118 keeps the cranial perforator centered, the perforator is pressed down against the skull so that inner drill 102 and connecting pin 242 are forced backwards against the pressure of spring 166. This action allows the inner drill's lugs 126 to enter recesses 222 of the rotating sleeve 202, so that the surfaces 128 of lugs 126 are engaged by the sleeve's surfaces 225B, with the result that rotation of the sleeve is imparted to the inner drill. As the inner drill rotates, its pyramidal projection 118 and its flutes 108 bore into the skull. At the same time, the outer drill's surfaces 159C are engaged by the rotating lugs' surfaces 134, causing the outer drill to rotate in unison with the inner drill. As the perforator cuts its way into the skull, the leading inner drill's flutes 108 cut a bore, and the trailing outer drill's flutes 260 cut a counterbore, so that a bore-counterbore opening is formed in the skull. Because front end surfaces 168 are cut at a flatter angle than front end surfaces 116, the outer drill will tend to encounter greater cutting resistance than the inner drill.

When the leading tip of the inner drill passes through the target bone, so that it no longer meets a resistive surface and is free to slip forward, the camming action of the outer drill's bevelled surfaces 159C bearing against the inner drill's lug surfaces 134 causes the inner drill to slip forward relative to the outer drill and the rear support and drive assembly far enough for lugs 126 to move out of recesses 222 and thereby disengage themselves from sleeve 202. With the inner drill no longer coupled to the rear support and drive unit 200, residual friction with the skull causes the rotation of drills 102 and 104 to cease. Further forward penetration of the cranial perforator is impeded at this point, inasmuch as the bore-counterbore made by the cranial perforator has formed a solid shoulder of bone which blocks the front surfaces 168 of the now-stationary outer drill. The cranial perforator may be removed from the cranial opening simply by pulling it backward.

On account of the number and shape of the inner drill's lugs 126 and the number and shape of the sleeve's lug-receiving recesses 222, and also on account of the manner in which connecting pin 242 is maintained within sleeve 202, the coupling between the front drill head assembly 100 and the rear support and drive assembly 200 provides reliable service during drilling even when the perforator is subjected to a variety of non-axial loadings. Three lugs 126 are provided so as to prevent wobbling of the inner drill, maintain positive locking of the inner drill to the sleeve 202 at all times when the perforator is pressed tightly against bone, and assure that de-clutching of the drill head assembly will occur automatically whenever the inner drill encounters a drop in resistance from the surface which it is drilling. Using two or four lugs for coupling the inner drill to the sleeve is undesirable since then there is a tendency for the inner drill to wobble, i.e., to shift laterally about a transverse pivot axis under non-axial loading. This wobbling action is detrimental since it creates a friction buildup between the inner and outer drills which may be great enough to prevent reliable de-clutching of the drill head assembly.

Because of the unique construction of the inner drill's flutes 108 and the outer drill's flutes 160, drilling can be conducted at relatively low speeds (i.e., at speeds of around 100 RPM), rather than at the relatively high speeds (i.e., speeds of around 800–1000 RPM) required of prior art devices in order for them to function properly.

Furthermore, the particular shapes of the inner drill's flutes 108 and the outer drill's flutes 160 enable removal of bone material from the cranial opening in a form best suited for subsequent repacking in the opening when the opening is closed at the conclusion of surgery.

The cranial perforator described and illustrated above is intended to be reused numerous times before being discarded. At the conclusion of the operation, the perforator may be easily disassembled for more complete cleaning. To accomplish disassembly, the front drill head assembly is rotated so that the attached connecting pin's radial bore 250 is aligned with the sleeve's radial bore 226. Then a tool is inserted into radial bores 226 and 250 so as to lock the connecting pin against rotation relative to sleeve 202. Thereafter, the front drill head assembly is unscrewed from the locked connecting pin, and the inner drill is separated from the outer drill. The three parts (i.e., the inner drill, the outer drill, and the rear support and drive assembly) may then be washed and sterilized. In this respect it is noted that the rear support and drive assembly generally requires no further disassembly for proper cleaning inasmuch as seal 228 prevents material from making its way into the rear portion of the support and drive assembly.

By carefully sizing the various parts of the cranial perforator so that front drill head assembly 100 cannot be screwed onto connecting pin 242 unless the inner drill's lugs 126 extend through the outer drill's slots 156, it is assured that the inner and outer drills can never be locked in position relative to one another so as to defeat the perforator's special "safety construction". Thus, reassembly of the cranial perforator after cleaning is rendered virtually foolproof.

Figure 9:
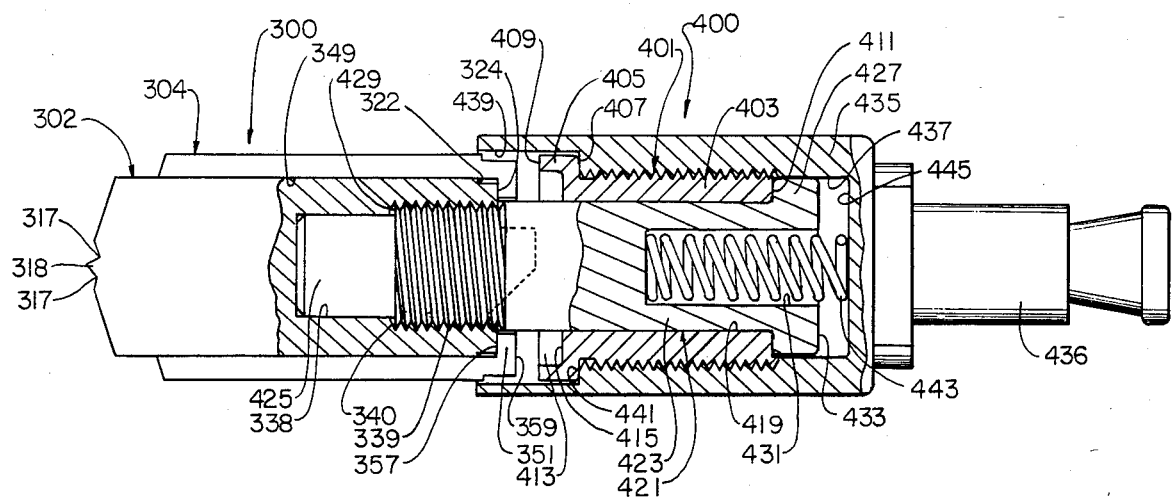
FIG. 9 is a side elevation, partially in section, of a disposable cranial perforator which comprises an alternative embodiment of the present invention.

FIGS. 9-12 show a disposable cranial perforator which comprises an alternative embodiment of the present invention. This alternative embodiment comprises a front drill head assembly 300 and a rear support and drive assembly 400 (FIG. 9). Front drill head assembly 300 comprises an inner drill 302 and an outer drill 304.

Inner drill 302 is shown in FIGS. 9, 10 and 12. Inner drill 302 is similar in shape to the inner drill 102 previously described. More particularly, the front end of inner drill 302 is identical to the front end of inner drill 102, inasmuch as the drill's cylindrical midsection 306 is dissected by a plurality of intersecting inclined surfaces so as to form three flutes 308 (FIG. 10). Specifically, the three flutes comprise a trio of first inclined surfaces 310, a trio of second inclined surfaces 312, and a trio of third inclined surfaces 314, plus a trio of end surfaces 316, with each of the latter being intersected by surfaces 310 and 312 of one flute and surface 314 of another flute. Flutes 108 are disposed 120 degrees apart from one another. Accordingly, each of the surfaces 310, 312 and 314 of each flute is displaced 120 degrees from the corresponding surface of the other two flutes. On account of the relative dispositions of inclined surfaces 310, 312, and 314, each of the flutes 308 has a front end notch 317, and the inner drill terminates in a pyramidal projection 318 which extends outward beyond the front end surfaces 316 of flutes 308 (FIGS. 9 and 10). The planes of surfaces 314 are eccentric to the lead point of pyramidal end projection 318, and end surfaces 316 are pitched at a $6\frac{1}{2}$ degree angle in the circumferential (i.e., non-radial) direction.

Inner drill 302 also comprises a cylindrical rear section 320 which is formed integral with cylindrical midsection 306. Cylindrical rear section 320 has a slightly smaller diameter than cylindrical midsection 306, so that an exterior shoulder 322 is formed at the intersection of these two sections (FIGS. 10 and 12). Cylindrical rear section 320 terminates in an end wall 324. A trio of lugs or keys 326 extend rearward from end wall 324. Lugs 326 are formed integral with cylindrical rear section 320 and are disposed 120 degrees apart from one another. Each of the lugs 326 is shaped so that it has a first side surface 328 which extends perpendicularly outward from end surface 324, an end surface 330 which extends substantially parallel to end surface 324, and a second side surface 332 which extends at an inclined angle (i.e., non-perpendicular) to end surface 324. A small groove 336 is formed in cylindrical rear section 320 at the intersection of each inclined side surface 332 and end surface 324.

Inner drill 302 also includes an axial bore 338 which begins at rear end surface 324 of cylindrical rear section 320 and extends into the middle of cylindrical midsection 306, and a threaded axial counterbore 339 which begins at rear end surface 324 of cylindrical rear section 320 and terminates at a shoulder 340 in the middle of midsection 306 (FIGS. 9 and 12).

Outer drill 304 is shown in FIGS. 9, 10 and 11. Outer drill 304 is similar to the outer drill 104 previously described. More particularly, outer drill 304 comprises a substantially cylindrical rear section 342 which is formed integral with a generally cylindrical front section 344. Front section 344 has a larger outside diameter than cylindrical rear section 342, and an exterior shoulder 346 is formed at their intersection. Cylindrical rear section 342 generally terminates in an end surface 348. An axial bore 349 passes through front section 344 and cylindrical rear section 342. Outer drill 304 also includes three lips or dogs 351 at its rear end. Lips 351 are formed integral with cylindrical rear section 342 and extend inwardly of rear section 342. Lips or dogs 351 are disposed 120 degrees apart from one another, and are sized and shaped so as to define a trio of radial extending slots 353 therebetween. Lips 351 terminate in arcuate inner surfaces 355, side surfaces 356A and 356B, and parallel opposite end surfaces 357 and 359.

The generally cylindrical front section 344 of outer drill 304 is dissected by a plurality of intersecting inclined surfaces so as to define three flutes or blades 360. More particularly, the three flutes 360 comprise a trio of first inclined surfaces 362, a trio of second inclined surfaces 364, and a trio of third inclined surfaces 366. Flutes 360 are disposed 120 degrees apart from one another, and each terminates in a front end surface 368. Front end surfaces 368 are pitched at a 3 degree angle in the circumferential (i.e., non-radial) direction.

Inner drill 302 and outer drill 304 are assembled in a concentric manner so as to form the complete front drill head assembly 300. More particularly, inner drill 302 and outer drill 304 are positioned in the manner shown in FIG. 10, i.e., so that the inner drill's flutes 308 are aligned with the outer drill's flutes 360, and so that the inner drill's lugs 326 are aligned with the outer drill's radial slots 353. Then the two drill members are brought together so that the inner drill slips inside and makes a close sliding fit with the outer drill, with the inner drill's end surface 324 coming to rest against the inner end surfaces 357 of the outer drill's lips 351 (FIG. 9). The various parts of the inner and outer drills are sized and shaped so that when the inner drill's end surface 324 engages the outer drill's inner end surfaces 357, and the lugs 326 are located in slots 353 so that the outer drill's front end surfaces 368 are in alignment with but rearward of the inner drill's front end surfaces 316, the outer drill's inclined surfaces 362 will form a rearward extension of the inner drill's inclined surfaces 310, the outer drill's inclined surfaces 364 will form a rearward extension of the inner drill's inclined surfaces 312, and the outer drill's inclined surfaces 366 will form a rearward extension of the inner drill's inclined surfaces 314. In addition, the inner drill's lugs 326 are sized so that when the inner drill's end surface 324 engages the outer drill's inner end surfaces 357, and the inner drill's flutes 308 are aligned with the outer drill's flutes 360, the lugs 326 will extend out through the outer drill's radial slots 353, with the first side wall surfaces 328 of the lugs extending parallel to and slightly spaced from side surfaces 356A of lips 351. The inner drill's lugs 326 are also sized so that they project out beyond the outer end surfaces 359 of the outer drill's lips 351 when the inner drill's end surface 324 engages the outer drill's inner end surfaces 357.

It is to be appreciated that the foregoing assembly can be achieved only if inner drill 302 and outer drill 304 are properly aligned with one another (i.e., so that the inner drill's lugs 326 are aligned with the outer drill's slots 353) prior to moving the two drills into engagement. More specifically, on account of the size and shape of lugs 326 and the size and shape of outer drill 304, if the lugs 326 are not properly aligned with the slots 353 when the two drill members are moved together, the end surfaces 330 of lugs 326 will encounter the inner end surfaces 357 of the outer drill's lips 351 and thereby prohibit the inner and outer drills from achieving the position shown in FIG. 9.

Rear support and drive assembly 400 is shown in FIG. 9. Assembly 400 comprises a hollow inner sleeve 401 having a threaded body section 403 and a substantially cylindrical collar section 405 at its front end. Collar section 405 has a larger outside diameter than body section 403, and an exterior shoulder 407 is formed at their intersection. Collar section 405 terminates in a front end surface 409, and body section 403 terminates in a rear end surface 411. A trio of key-receiving recesses 413 are formed in the sleeve's front end surface 409. Recesses 413 are similar in shape to the aforementioned openings 222 formed in the aforementioned rear support and drive assembly 200, and are spaced 120 degrees apart from one another. Recesses 413 have bottom surfaces 415. The axial bore in sleeve 401 is identified by numeral 419.

A coupling or connecting pin 421 is slidably disposed within sleeve 401. Connecting pin 421 has a cylindrical midsection 423, a cylindrical front section 425 having a reduced diameter relative to cylindrical midsection 423, and a rear flange 427 having an enlarged diameter relative to cylindrical midsection 423. A shoulder 429 is formed at the intersection of cylindrical front section 425 and cylindrical midsection 423. Cylindrical midsection 423 is threaded for a short distance rearward of shoulder 429. Connecting pin 421 is sized so that its cylindrical midsection 423 makes a close sliding fit in bore 419 of sleeve 401, in order that connecting pin 421 will be capable of independent movement relative to sleeve 401. Connecting pin 421 also includes an axial bore 431 extending forward from the rear end surface 433 of rear flange 427.

Means are provided to urge connecting pin 421 forward so that the pin's rear flange 427 normally engages the rear end surface 411 of inner sleeve 401, in the manner shown in FIG. 9. More particularly, the rear support and drive unit 400 includes a drive adaptor 435 which fits over sleeve 401. Adaptor 435 has a rear section 436 having a stepped-down outer configuration adapted to be received by a Hudson chuck. Adaptor 435 includes an axial bore 437, an axial counterbore 439, and a shoulder 441 formed at the intersection of bore 437 and counterbore 439. Counterbore 439 is threaded for a distance rearward of shoulder 441 so as to permit the adaptor to be screwed onto sleeve 401, with the threaded sleeve's collar section 405 fitting in counterbore 439 and the sleeve's shoulder 407 engaging the adaptor's shoulder 441. A compression spring 443 is located in the connecting pin's bore 431 so as to urge the connecting pin forward away from the adaptor's interior end surface 445 and thus keep flange 427 of the connecting pin biased against the inner sleeve's rear end surface 411. This construction suffices to keep the connecting pin's rear flange 427 biased against the inner sleeve's end surface 411 without significantly impeding rotation of connecting pin 421 relative to sleeve 401. At the same time, pin 421 is capable of axial motion relative to sleeve 401 to the extent permitted by the gap normally extending between flange 427 and end surface 445.

As a consequence of the foregoing construction, it will be appreciated that rear support and drive unit 400 essentially forms a self-contained unit wherein connecting pin 421 projects its threaded front end outward from inner sleeve 401 and adaptor 435 and is yieldably biased into that position, and further wherein the connecting pin is capable of independent rotation relative to sleeve 401 and adaptor 435.

The front drill head assembly 300 is united with the rear support and drive assembly 400 by screwing connecting pin 421 into the inner drill's bore 338 and threaded counterbore 339, until the connecting pin's shoulder 429 seats on the inner drill's shoulder 340. The various parts of the disposable cranial perforator are sized so that when spring 443 is holding the connecting pin's rear flange 427 against the rear end surface 411 of inner sleeve 401, the inner drill's lugs 326 will terminate short of the sleeve's front end surface 409. At the same time, however, the various parts of the cranial perforator are sized so that when the inner drill is forced back towards rear support and drive assembly 400, lugs 326 can extend into the lug-receiving recesses 413 formed in sleeve 401 and the rear end surface 359 of outer drill 304 can engage the front end surface 409 of sleeve 401, before the rear end surface 433 of the connecting pin contacts end surface 445. Adaptor 435 is sized so that when the front drill head assembly is united with the rear support and drive assembly, the front end of the adaptor will extend over the rear end of the front drill head assembly in the manner shown in FIG. 9.

The adaptor 435 is made to extend over the rear end of the front drill head assembly for a most important reason; specifically, this construction makes it impossible for an assembled perforator to be disassembled, with the result that reuse of the perforator is effectively prohibited so long as sterile conditions are a requisite. Disassembly is prevented inasmuch as the freely rotating connecting pin 421 must be held stationary in order for the front drill head assembly to be detached from the remainder of the perforator, and the connecting pin is rendered inaccessible on account of the fact that inner sleeve 401 is also inaccessible and therefore cannot be held still to allow for the unscrewing of adaptor 435 from sleeve 401.

To further inhibit reuse of the disposable cranial perforator, adaptor 435 may be formed of a low temperature thermoplastic so that the adaptor will destruct in a high-temperature autoclave during a sterilization procedure. Adaptor 435 also may carry a gas-sensitive label on its exterior surface to indicate whether the perforator has been subjected to a gas sterilization procedure.

Operation of the disposable cranial perforator is substantially the same as the operation of the reusable cranial perforator, and hence need not be redescribed.

Figure 13:
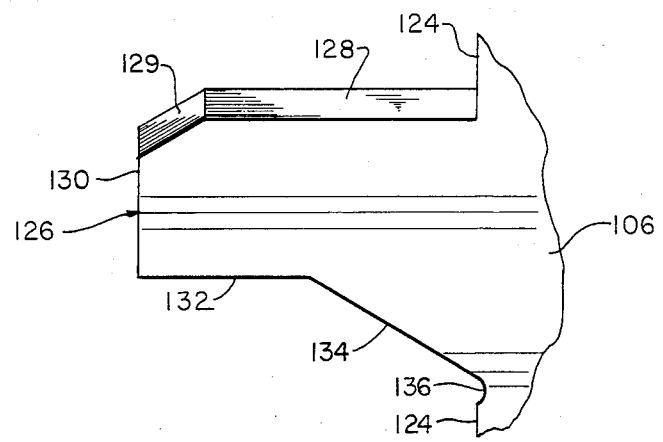
FIG. 13 is an enlarged fragmentary showing an alternative embodiment of the inner drill's lugs.

FIG. 13 shows an alternative embodiment of the inner drill's lugs 126. In this case, a corner of each lug 126 is bevelled so as to provide a planar surface 129 which is interposed between and extends at an inclined angle (i.e., non-perpendicular) to both side surface 128 and end surface 130. Surfaces 129 serve as cam surfaces. They are engaged by the sleeve's surfaces 225B (FIG. 5) as the inner drill slips forward at the conclusion of drilling and such engagement assists forward movement of the inner drill relative to sleeve 202 and thereby promotes a more rapid disengagement of the inner drill's lugs 126 from sleeve 202.

Advantages Of The Invention

Numerous advantages are obtained by using the present invention.

First, the present invention provides a cranial perforator having a reliable "safety construction" designed to permit forward penetration by the perforator only so long as the perforator's leading tip is encountering hard bone, and to halt forward penetration by the perforator as soon as the perforator's leading tip passes through the hard bone and before it encounters the soft tissue beneath the bone.

Second, the present invention provides a cranial perforator having an improved clutch means for coupling the front drill head assembly to the rear support and drive assembly, the clutch means being designed so as to assure automatic de-clutching even when the perforator is manipulated under non-axial loads.

Third, the present invention provides a cranial perforator which includes a uniquely formed centering point to assist in centering the perforator when starting a bore, so as to minimize the tendency of the perforator to skate across the skull.

Fourth, the flutes of the cranial perforator of this invention are well adapted to remove the skull material from the cranial opening in a form best suited for subsequent repacking in the opening when the opening is closed at the conclusion of surgery.

Fifth, the invention provides a cranial perforator which can be used with relatively low speed drills (i.e., drills operating at speeds of around 100 RPM), as well as with relatively high speed drills (i.e., drills operating at speeds of around 800-1000 RPM).

Sixth, the present invention provides a reusable cranial perforator better adapted to withstand repetitive non-axial loading, so that the perforator will not tend to fail after an indefinite period of use.

Seventh, the present invention provides a reusable cranial perforator which has a long operational lifetime, and which is easy to disassemble and to reassemble so as to facilitate cleaning.

Eighth, the present invention provides a reusable cranial perforator which disassembles into relatively few pieces, so as to facilitate disassembly and reassembly.

Ninth, the present invention provides a reusable cranial perforator which will be rendered totally inoperative if it is reassembled incorrectly.

Tenth, the present invention provides a disposable cranial perforator which cannot be disassembled without rendering the perforator totally inoperative.

Eleventh, the present invention provides a disposable cranial perforator which will indicate when it has been resterilized in an attempt to use it more than once.

Finally, the invention has the advantage that it is susceptible of modifications other than those already described. Thus, the shapes of the cutting flutes may be changed. Still other possible modifications will be obvious to persons skilled in the art. Whst I claim is:

1. A drilling implement for drilling holes in bone structure comprising a drill head assembly and a drill head drive assembly;

said drill head assembly comprising a hollow outer drill member and an inner drill member coaxially disposed within said outer drill member;

said outer drill member comprising an outer end having a plurality of cutting flutes and an inner end having three circumferentially-spaced lips that extend in a plane at right angles to the longitudinal axis of said outer drill member, each of said lips having a drive surface extending in a plane that intersects the plane of said lips;

said inner drill member comprising an outer end having a plurality of cutting flutes and an inner end having (1) an end surface, (2) three circumferentially-extending, mutually-spaced lugs projecting from said end surface parallel to the center axis of said inner drill member, each of said lugs having a cam surface extending circumferentially and at an angle to the longitudinal axis of said inner drill member and disposed to engage one of said drive surfaces and thereby drive said outer drill member when said inner drill member is rotated in a first direction, and (3) a threaded center hole;

said drill head drive assembly comprising a drive member, a drill head/drill drive coupling member, a drive adaptor, and biasing means;

said drive member comprising an end surface extending transversely of its axis and interrupted by three recesses for receiving said three lugs, each of said recesses being defined in part by side surfaces extending in planes extending parallel to the center axis of said drive member;

said coupling member being screwed into said threaded center hole so that is and said inner drill member will rotate as a unit when said inner drill member is rotated in a said first direction;

said drive adaptor being connected to said drive member so that said drive adaptor and said drive member will rotate as a unit when said drive adaptor is rotated in said first direction; and said biasing means being disposed so as to bias said coupling member and said inner drill member axially away from said drive adaptor;

said drill head assembly and said drill head drive assembly being arranged so that when said drive adaptor is rotated in said first direction, (a) so long as said inner drill member encounters a predetermined resistance to penetration, said lugs will remain engaged with said side surfaces and said inner drill member will cause said outer drill member to rotate with it as a unit with said drive adaptor, and (b) when said inner drill member no longer encounters said predetermined resistance to penetration, said cam surfaces will coact with said drive surfaces to force said inner drill member forward relative to said outer drill member and said drill head drive assembly sufficiently for said lugs and said side surfaces to be disengaged, whereby said inner and outer drill members will slip relative to said drive member as said drive adaptor is rotated in said first direction.

2. An improved drilling implement according to claim 1 wherein said adaptor has a tubular front section which surrounds said drive member and overlaps said inner end of said outer drill member.

3. An improved drilling implement according to claim 1 wherein said inner drill member has a plurality of shaped flutes with cutting edges, with each flute characterized by a plurality of prismatically disposed surfaces, a front cutting edge on the forward end of said each flute, and a longitudinally-extending cutting edge formed by the intersection of one of said prismatically disposed surfaces and the outer surface of said inner drill member, and further wherein said inner drill member comprises a three-sided pyramidal center point which projects forwardly of said front cutting edges, and a notch in each flute separating the said front cutting edge of said flute from said pyramidal center point.

4. An improved drilling implement according to claim 1 wherein said inner drill member has a plurality of shaped flutes, with each flute characterized by a plurality of prismatically disposed surfaces, a front cutting edge on the forward end of said each flute, and a longitudinal cutting edge formed by the intersection of one of said prismatically disposed surfaces and the outer surface of said inner drill member, and further wherein said one prismatically disposed surface is formed so that it is eccentric to the center axis of said inner drill member.

5. An improved drilling implement according to claim 4 wherein said inner drill member has front end surfaces terminating in said front cutting edges, and said outer drill member has matching flutes each having a front end surface terminating in a front cutting edge, and further wherein the front end surfaces of said inner and outer drill members are disposed at different angles to the longitudinal axis of said drilling implement.

6. An improved drilling implement for drilling holes in bone structure comprising:
   a drill head assembly and a drill head drive assembly coupled to said drill head assembly so as to selectively cause said drill head assembly to be drivingly engaged by or disengaged from said drill head drive assembly;
   said drill head assembly comprising an inner drill member, an outer drill member, and means for coupling said inner drill member to said drill head drive assembly;
   said drive head drive assembly comprising a drive member, a coupling member, a drive adaptor, and a biasing means;
   said inner drill member having a first end with shaped drilling flutes terminating in cutting edges, and a second end with a plurality of circumferentially spaced lugs projecting from said second end parallel to the axis of said inner drill member;
   said lugs each having a cam surface extending in a plane that is inclined relative to the longitudinal axis of said inner drill member;
   said outer drill member being hollow and rotatably surrounding said inner drill member, said outer drill member having a first end with shaped drilling flutes terminating in cutting edges, and a second end with a plurality of dogs and spaces between said dogs sized to permit said lugs to project between said dogs;
   said dogs each having a bevelled surface in position to engage one of said cam surfaces and urge said inner drill member axially forward relative to said outer drill member and said drive member when said inner drill member is being rotated in a selected direction;
   said drive member being hollow and having a limit surface extending transversely of the axis of rotation of said drilling implement, and a plurality of recesses in said limit surface for accommodating said lugs;
   said coupling member extending through said drive member and being secured to said inner drill member, said coupling member being rotatable relative to said drive member and being capable of axial movement between a first limit position in which said lugs are disposed in said recesses and a second limit position in which said lugs are clear of said recesses;
   said drive adaptor being secured to said drive member so as to cause said drive member to rotate with said drive adaptor; and
   said biasing means being disposed between said drive adaptor and said coupling member so as to urge said coupling member to said second limit position, whereby (a) said drill head assembly will be free to rotate relative to said drive assembly if said inner drill member is not subjected to an axially-applied force directing it toward said drive adaptor and (b) said drill head assembly will be locked to said drive assembly for rotation therewith when said inner drill member is forced toward said drive adaptor far enough to place said coupling member in said first limit position.

7. An improved drilling implement according claim 6 wherein said inner and outer drill members each has three flutes.

8. An improved drilling implement according to claim 6 wherein said inner drill member is characterized by a plurality of shaped drilling flutes with cutting edges, each of said flutes having a plurality of prismatic surfaces, a front cutting edge on the forward end of each of said shaped drilling flutes, a pyramidal center point which projects forwardly of said front cutting edges, and a notch in each of said shaped drilling flutes separating said front cutting edges from said pyramidal center point.

9. An improved drilling implement according to claim 6 wherein said adaptor member is coupled to said drive member by a screw thread connection.

10. An improved drilling implement according to claim 6 wherein said lugs are formed with first surfaces extending parallel to the longitudinal axis of said drilling head and second surfaces extending at an acute angle to said axis, and said limit surface has selected edge surfaces defining the opposite sides of said recesses which extend parallel to said longitudinal axis, whereby when said first surfaces are engaged with said selected edge surfaces, said inner drill member will be driven by said drive member as said drive member is rotated in said first direction.

11. An improved drilling implement according to claim 6 wherein each of said lugs is bevelled on one end corner.

12. An improved drilling implement according to claim 6 wherein said drive member and said coupling member are separated and supported by at least one roller-type bearing member.

13. An improved drilling implement according to claim 12 wherein said inner drill member has three lugs and said drive member has three recesses for receiving said three lugs.

14. An improved drilling implement for drilling holes in bone structures comprising:
   a drill head assembly and a drill head drive assembly coupled to said drill head assembly so as to selectively cause said drill head assembly to be drivingly engaged by or disengaged from said drill head drive assembly;
   said drill head assembly comprising an inner drill member, an outer drill member, and means for coupling said inner drill member to said drill head drive assembly;
   said drill head drive assembly comprising a drive member, a coupling member, a drive adaptor, a biasing means, and bearing means;
   said inner drill member having a first end with shaped drilling flutes terminating in cutting edges, and a second end with circumferentially spaced lugs projecting from said second end parallel to the axis of said inner drill member;
   said lugs each having a cam surface extending in a plane that is inclined relative to the longitudinal axis of said inner drill member;

said outer drill member hollow and rotatably surrounding said inner drill member, said outer drill member having a first end with shaped drilling flutes terminating in cutting edges, and a second end with dogs and spaces between said dogs sized to permit said lugs to project between said dogs;

said dogs each having a surface in position to engage one of said cam surfaces and urge said inner drill member axially forward relative to said outer drill member and said drive member when said inner drill member is being rotated in a selected direction;

said drive member being hollow and having a limit surface extending transversely of the axis of rotation of said drilling implement, and recesses in said limit surface for accommodating said lugs;

said coupling member extending through said drive member and being secured to said inner drill member, said coupling member being rotatable relative to said drive member and being capable of axial movement between a first limit position in which said lugs are disposed in said recesses and a second limit position in which said lugs are clear of said recesses;

said drive adaptor being secured to said drive member so as to cause said drive member to rotate with said drive adaptor;

said biasing means being disposed between said drive adaptor and said coupling member so as to urge said coupling member to said second limit position, whereby (a) said drill head assembly will be free to rotate relative to said drive assembly if said inner drill member is not subjected to an axially-applied force directing it toward said drive adaptor and (b) said drill head assembly will be locked to said drive assembly for rotation therewith when said inner drill member is forced toward said drive adaptor far enough to place said coupling member in said first limit position; and said bearing means being disposed between said drive member and said coupling member so as to facilitate rotation of said drive member relative to said coupling member.

15. An improved drilling implement according to claim 14 further including sealing means between said drive member and said coupling member for preventing introduction of foreign matter into said bearing means.

16. An improved drilling implement according to claim 14 further including a mandrel connected to said drive adaptor, and further wherein said biasing means is a coiled spring having one end mounted on said mandrel.

17. A drilling implement for drilling holes in bone structures comprising a drill head assembly and a drill head drive assembly;

said drill head assembly comprising a hollow outer drill member and an inner drill member coaxially disposed within said outer drill member;

said outer drill member comprising an outer end having a plurality of cutting flutes and an inner end having a plurality of circumferentially-spaced lips that extend in a plane at right angles to the longitudinal axis of said outer drill, each of said lips having a drive surface extending in a plane that intersects the plane of said lips;

said inner drill member comprising an outer end having a plurality of cutting flutes and an inner end having (1) an end surface, (2) a plurality of mutually-spaced, circumferentially-extending lugs projecting from said end surface parallel to the longitudinal axis of said inner drill member, each of said lugs having a cam surface extending circumferentially and at an angle to the longitudinal axis of said inner drill member and disposed to engage one of said drive surfaces and thereby drive said outer drill member when said inner drill member is rotated in a first direction, and (3) a threaded center hole;

said flutes of said inner drill member having front end surfaces terminating in front cutting edges and said flutes of said outer drill member having front end surfaces terminating in front cutting edges, with said front end surfaces of said outer drill member being disposed at a shallower angle to the longitudinal axis of said drilling implement than said front end surface of said inner drill member, whereby said outer drill member will encounter greater resistance to cutting than said inner drill member;

said drill head drive assembly comprising a drive member, a drill head/drill drive coupling member, a drive adaptor, and biasing means;

said drive member comprising an end surface extending transversely of its axis and interrupted by a plurality of recesses for receiving said plurality of lugs, each of said recesses being defined in part by side surfaces extending in planes extending parallel to the center axis of said drive member;

said coupling member being screwed into said threaded center hole so that it and said inner drill member will rotate as a unit when said inner drill member is rotated in a said first direction;

said drive adaptor being connected to said drive member so that said drive adaptor and said drive member will rotate as a unit when said drive adaptor is rotated in said first direction; and said biasing means being disposed so as to bias said coupling member and said inner drill member axially away from said drive adaptor;

said drill head assembly and said drive assembly being arranged so that when said drive adaptor is rotated in said first direction, (a) so long as said inner drill member encounters a predetermined resistance to penetration, said lugs will remain engaged with said side surfaces and said inner drill member will cause said outer drill member to rotate with it as a unit with said drive adaptor, and (b) when said inner drill member no longer encounters said predetermined resistance to penetration, said cam surfaces will coact with said drive surfaces to force said inner drill member forward relative to said outer drill member and said drill head drive assembly sufficiently for said lugs and said side surface to be disengaged, whereby said inner and outer drill members will slip relative to said drive member as said drive adaptor is rotated in said first direction.

18. A drilling implement for drilling holes in bone structures comprising a drill head assembly and a drill head drive assembly;

said drill head assembly comprising a hollow outer drill member and an inner drill member coaxially disposed within said outer drill member;

said outer drill member comprising an outer end having a plurality of cutting flutes and an inner end having three circumferentially-spaced lips that extend in a plane at right angles to the longitudinal axis of said outer drill, each of said lips having a drive surface extending in a plane that intersects the plane of said lips and said longitudinal axis;

said inner drill member comprising an outer end having a plurality of cutting flutes and an inner end having (1) an end surface, (2) three mutually-spaced, circumferentially-extending lugs projecting from said end surface parallel to the longitudinal axis of said inner drill member, each of said lugs having a cam surface extending circumferentially and at an angle to the longitudinal axis of said inner drill member and disposed to engage one of said drive surfaces and thereby drive said outer drill member when said inner drill member is rotated in a first direction, and (3) a threaded center hole;

said flutes of said inner drill member having front end surfaces terminating in front cutting edges and said flutes of said outer drill member having front end surfaces terminating in front cutting edges, with said front end surfaces of said outer drill member being disposed at a shallower angle to the longitudinal axis of said drilling implement than said front end surface of said inner drill member, whereby said outer drill member will encounter greater resistance to cutting than said inner drill member;

said inner drill member also having a pyramidal center point characterized by three converging sides projecting forwardly from said front end surfaces;

said drill head drive assembly comprising a drive member, a drill head/drill drive coupling member, a drive adaptor, and biasing means;

said drive member comprising an end surface extending transversely of its axis and interrupted by three recesses for receiving said three lugs, each of said recesses being defined in part by side surfaces extending in planes extending parallel to the center axis of said drive member;

said coupling member being screwed into said threaded center hole so that it and said inner drill member will rotate as a unit when said inner drill member is rotated in a said first direction;

said drive adaptor being connected to said drive member so that said drive adaptor and said drive member will rotate as a unit when said drive adaptor is rotated in said first direction;

said biasing means being and disposed so as to bias said coupling member and said inner drill member axially away from said drive adaptor;

said drill head assembly and said drive assembly being arranged so that when said drive adaptor is rotated in said first direction, (a) so long as said inner drill member encounters a predetermined resistance to penetration, said lugs will remain engaged with said side surfaces and said inner drill member will cause said outer drill member to rotate with it as a unit with said drive adaptor, and (b) when said inner drill member no longer encounters said predetermined resistance to penetration, said cam surfaces will coact with said drive surfaces to force said inner drill member forward relative to said outer drill member and said drill head drive assembly sufficiently for said lugs and said side surfaces to be disengaged, whereby said inner and outer drill members will slip relative to said drive member as said drive adaptor is rotated in said first direction.

* * * * *

UNITED STATES PATENT AND TRADEMARK OFFICE
CERTIFICATE OF CORRECTION

PATENT NO. : 4,600,006
DATED : July 15, 1986
INVENTOR(S) : John W. Baker

It is certified that error appears in the above-identified patent and that said Letters Patent is hereby corrected as shown below:

Claim 1, column 15, line 51, the word "structure" should be changed to -- structures --;

Claim 1, column 16, line 19, the word "a" should be deleted;

Claim 6, column 17, line 14, the word "structure" should be changed to -- structures --;

Claim 17, column 20, line 54, the word "surface" should be changed to -- surfaces --; and Claim 18, column 22, line 11, the word "and" should be inserted after the semicolon.

Signed and Sealed this

Third Day of February, 1987

Attest:

DONALD J. QUIGG

Attesting Officer

Commissioner of Patents and Trademarks